United States Patent [19]

Mensink

[11] 4,304,237

[45] Dec. 8, 1981

[54] DUAL MODE PROGRAMMABLE PACER

[75] Inventor: Kornelis A. Mensink, Brummen, Netherlands

[73] Assignee: Vitatron Medical B.V., Dieren, Netherlands

[21] Appl. No.: 955,908

[22] Filed: Oct. 30, 1978

[51] Int. Cl.³ .............................................. A61N 1/36
[52] U.S. Cl. ............................................ 128/419 PG
[58] Field of Search ................... 128/419 PG, 419 PT

[56] References Cited

U.S. PATENT DOCUMENTS 3,777,762 12/1973 Nielsen ......................... 128/419 PT
4,066,086 1/1978 Alferness et al. ............. 128/419 PG

*Primary Examiner*—William E. Kamm

*Attorney, Agent, or Firm*—Woodcock, Washburn, Kurtz, Mackiewicz & Norris

[57] ABSTRACT

There is provided a programmable pacer which is adapted to be programmed from an external source in either a slow program mode, wherein the external source is a simple magnet, or a fast program mode wherein the external programming signals are generated automatically and comprise a constant magnetic signal along with a modulated relatively high frequency magnetic signal. The pacer has means for receiving both fast and slow type program signals and means for processing the received program signals, whether of the fast or slow type, to derive control signals therefrom when the program signals conform to a predetermined program arrangement.

11 Claims, 3 Drawing Figures

DUAL MODE PROGRAMMABLE PACER

BACKGROUND OF THE INVENTION

This invention relates to cardiac pacers, and, more particularly, implantable cardiac pacers adapted to be programmed by the use of externally generated signals for changing operating parameters of the pacer. This application relates to U.S. Pat. No. 4,124,031, assigned to the same assignee, which covers an implantable programmable pacer incorporating a logic system for receiving magnetic signals from a simple magnet source, which patent is incorporated herein by reference.

With new improved power sources now being used in the pacer industry, such as the lithium battery, as well as advanced techniques for providing long life reliability and low current drain in more complex circuits, programmable pacers are coming into increasing use. Such use to date of programmable pacers has indicated what the most important design features are. Of course, for any implanted biomedical device, it must be reliable. Reliability in turn is tied to simplicity of design and low power operation. Another important design consideration is that the pacer be immune from being accidentally programmed by unwanted external signals which may be in the environment of the patient. At the same time, the physician who treats the patient desires to have a pacer which can be easily and simply programmed, as by an automatic transmitter which is set by simply pushing several buttons, and without requiring any complicated procedure on behalf of the physician. Also, and particularly in view of the fact that the pacer may be implanted for a lifetime of perhaps up to 15 years, it is important that the pacer have a fallback or "fail-safe" means of being programmed in the event that the automatic transmitter is not available when neded.

A programming system for an implanted pacer has been provided, as disclosed in U.S. Pat. No. 4,124,031, which utilizes a simple magnet providing a constant magnetic field which is capable of penetrating the sealed pacer housing. The pacer is programmed when the physician places the magnet in the vicinity of the patient's implanted pacer for time periods which correlate with the patient's heartbeat in accordance with a predetermined program arrangement. The externally applied magnetic field activates a reed switch, the closing and opening of which in accordance with the predetermined program arrangement is detected, so as to initiate a change of a given pacer parameter in accordance with the predetermined program. This arrangement provides essentially the safest form of programming in terms of availability, since simple magnets are universally available, are found in all parts of the world, and can be expected to be found indefinitely into the future.

While simple magnet programming provides the advantages as set forth above, many physicians will not want to use a simple magnet because this would require that they follow a predetermined specific procedure in order to achieve proper programming. Physicians understandably in many instances would prefer an automatic external programmer, or transmitter, whereby the desired parameter is set in, as in a pushbutton keyboard, and then the program-encoded signals are transmitted automatically to the pacer. For the physician who will always be in his office or otherwise at a location where the programmer-transmitter is always available, he will certainly prefer the automatic transmitter as opposed to the manual procedure using a simple magnet.

Thus, there are good arguments in favor both of a programmable pacer adapted to be programmed by a simple magnet, and of an automatic transmitter. Ideally, the best solution would be to have both arrangements. However, the circuitry within the pacer for decoding programming signals is inherently complex, adding to the expense of the device. Extra circuitry also requires consumption of power and contributes to energy depletion of the battery source and thus contributes to a shortened pacer lifetime. In terms of reliability, the use of parallel programming systems would aid in ensuring that the patient can always be reprogrammed in one way or the other. However, many practicalities of the pacer design would dictate against parallel programming systems. For example, it is desirable to contain the pacer electronics on one or at most two chips, and a design that would mean adding an extra chip simply would not be acceptable.

The objectives of this invention are to overcome the disadvantages of the prior art programmable pacers. Since each prior art programmable pacer utilizes its own programming arrangement, i.e., own form of encoding the transmitted signals, the patient who carries such a programming pacer can be reprogrammed only with the specific programmer designed for use with the model pacer being worn. For this reason there is no reliable form of backup transmitter for providing programming in the event that the specific automatic programmer is not available. On the other hand, the pacer which has the capacity for programming one or more operating parameters by simple manipulation of a magnet carries the disadvantage of being vulnerable to extraneous signals, such that it is not secure, and even if made secure is in disfavor compared to automatic pacers because of the physician's desire for an automatic transmitter which obviates the physician's having to master the programming procedure. These disadvantages of the prior art are overcome by applicant's invention, wherein there is provided a pacer adapted to be programmed either by slow program signals (provided by a simple magnet) or fast program signals (provided by an automatic transmitter). The pacer of this invention provides additional advantages of reliability and cost reduction, as well as reduced power drain, by providing a common logic circuit, or program decoding circuit, which is compatible for accepting and analyzing both the fast and slow program signals. There is thus provided a pacer which overcomes the disadvantages of prior art pacers without requiring any significant additional complexity, being reliably programmable by an automatic external programmer or by the fail-safe backup method of using a simple magnet to provide the program signals. For decoding the fast program signals, the pacer utilizes a unique circuit for detecting the envelope of a modulated magnetic signal, the circuit providing both an envelope detector and a sharp bandpass filter characteristic.

DESCRIPTION OF THE PREFERRED EMBODIMENTS

Figure 1:
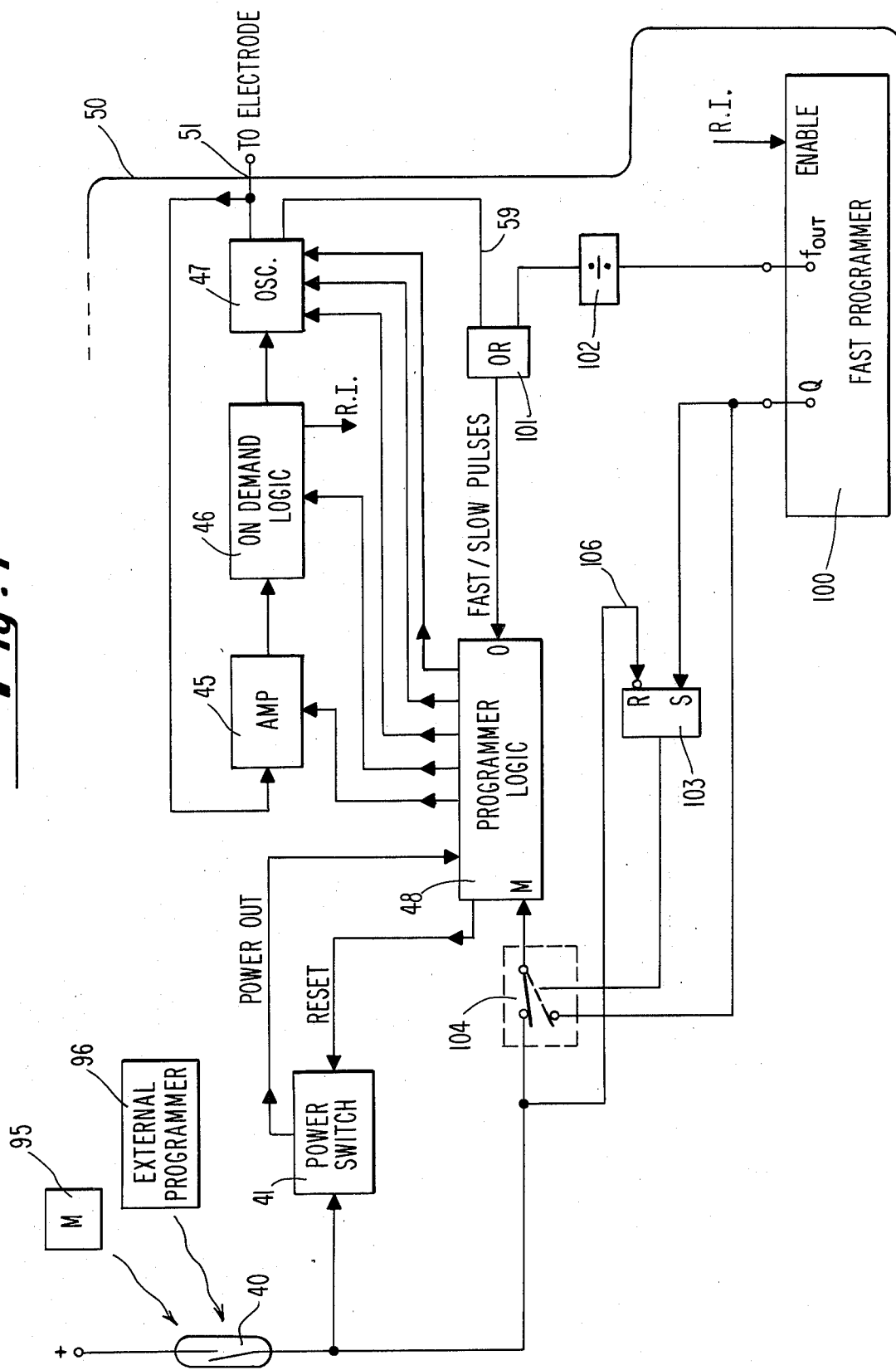
FIG. 1 is a block diagram showing the primary components of the pacer of this invention, and in particular showing the circuit arrangement providing for dual programming compatibility whereby the pacer is programmable by program signals delivered at relatively different rates.

Referring now to FIG. 1, there is shown an overall block diagram of a pacer embodying this invention. The pacer is suitably encased in a sealed titanium case as shown at 50. The pacer is illustrated as a demand pacer, and includes an amplifier circuit 45 which detects and amplifies detected QRS signals. The output of amplifier 45 is transmitted to on-demand logic 46, which performs conventional pacer functions such as determining whether the amplified signal represents a natural QRS signal or a delivered stimulus pulse, determining whether noise is present, timing out the refractory interval (RI), etc. When a natural signal has been detected, logic circuit 46 outputs a reset signal to oscillator 47. Oscillator 47 is a conventional stimulus pulse generator, which is adaptable to be programmed as to rate, pulse width, pulse amplitude, etc. Signals which are delivered from oscillator 47 are outputted through feedthrough element 51 which passes through the pacer case 50, for connection to an appropriate electrode for delivery to the patient's heart.

The pacer is adapted for external programming in accordance with the disclosure in U.S. Pat. No. 4,124,031, assigned to the same assignee, which application is incorporated by reference. The operating parameters of the pacer which are programmable are modified by signals generated in programmer logic circuit 48, which is shown having outputs connected to amplifier 45 (for controlling sensitivity), demand logic circuit 46 and oscillator 47. The details of an illustrative programmer logic circuit are presented in the aforementioned U.S. Pat. No. 4,124,031. For this application, it need only be mentioned that the programmer logic circuit 48 receives two signals, which are inputted at the terminals designated M and O respectively. For "slow" programming, the input at M represents the presence of a magnetic signal received from an external source, and the input at O represents an output from oscillator 47; for fast programming, the input at M represents the envelope of the modulation on the received external signal while the input at O represents the output of the programmer oscillator $f_{out}$ (which is suitably a 600 Hz signal).

Conventional reed switch 40 is shown as providing a connection from a + voltage source to a power switch 41 when the reed switch is closed due to the presence of an external magnetic field. A closing of switch 40 causes the setting of a flip-flop within switch block 41 for connection power along the line designated POWER OUT to programmer logic circuit 48. Logic circuit 48 is provided with power until some time after removal of the magnetic field from the vicinity of switch 40, at which time logic circuit 48 provides a reset signal which resets switch circuit 41. The signal from switch 40 is also normally connected through switch 104 to the M input terminal of programmer logic circuit 48. For slow programming, where the external magnetic field is supplied by a hand held magnet 95, this is always the case. At the same time, in this slow mode, output signals from oscillator 47, which are generated either when the oscillator times out or when it is reset, are connected through OR gate 101 to the O terminal of the programmer logic. In this case, programmer logic 48 responds to the coincidence of the slow oscillator pulses received at terminal O with the magnetic signal which is received at terminal M, as described in detail in the aforementioned U.S. Pat. No. 4,124,031.

For fast programming, provided by external programmer 96, the inputs to programmer logic circuitry 48 are provided by the fast programmer circuit 100. External programmer 96 provides a high speed programmed magnetic signal which comprises a constant level magnetic signal of sufficient strength to maintain switch 40 closed for the duration of the signal. At the same time, there is provided amplitude modulation of the magnetic signal at a selected frequency on the order of 600 Hz. This frequency is a matter of design choice, and it is understood that the invention is in no way limited to the exact choice of this frequency or the exact nature of the modulation provided. When the 600 Hz magnetic signal is present, it is detected by circuit 100, which circuit provides two outputs which are connected to the M and O terminals respectively of programmer logic circuitry 48. During the refractory interval the circuit 100 is enabled by the RI signal from circuit 46. When a fast programming signal is sent from external programmer 96, detected 600 Hz modulation causes a ring oscillator within circuit 100 to produce an output $f_{out}$ which lasts for the duration of the refractory interval. This signal is gated through OR gate 101 to the O input of the circuitry 48. As desired, the $f_{out}$ signal may be divided and/or delayed by conventional circuitry as shown at 102. Circuit 100 also provides, at terminal Q, an envelope signal which is a logic 1 during the presence of the 600 Hz modulation and a logic 0 during the absence of such modulation. This signal is connected through switch 104 to the M input. Switch 104 is changed to connect fast programmer circuit 100 to the M input by the connection of the Q output to the set terminal of flip-flop 103 which, when set, produces a signal which switches switch circuit 104. Flip-flop 103 can be so set when and only when the constant magnetic field from external programmer 96 holds reed switch 40 closed, so that the flip-flop is not reset by the signal on line 106. It is seen that if the reed switch opens, a 0 logic signal appears on line 106 which causes resetting of flip-flop 103, thereby returning switch 104 to its normal position.

The dual nature of either fast or slow programming can now be appreciated. For slow programming, done by manual application of the magnet as indicated at 95, the programmer logic compares the signal at input M, which represents presence of the magnet, with the occurrence of oscillator (slow) pulses from oscillator 47. In this mode, the doctor enters the programming signal by application of the magnet and removal of the magnet for periods of time corresponding to predetermined pacer oscillator pulse groupings, as set forth in U.S. Pat. No. 4,124,031. By counting patient heartbeats, which correspond to the slow pulses, the doctor can apply and remove the magnet for the required time intervals so as to properly program the pacer. For fast programming, which occurs during the refractory interval between successive actual heartbeats, the magnetic signal is supplied by the detected envelope of the programmed external signal, while the oscillator pulses are provided by the relatively fast (e.g., 600 Hz) output signals from the fast programmer. In this case, the time relationship of the envelope and the 600 Hz signals is predetermined by the external programmer, such that the doctor does not need to do anything to ensure the proper programming except to dial in the desired programming information to unit 96. Thus, there is provided a system for dual mode programming, e.g., both slow and fast. Generally the fast programming will be preferred, since it is automatic, but it is important that means also be provided for the slow programming in situations where only a magnet is available.

Figure 2:
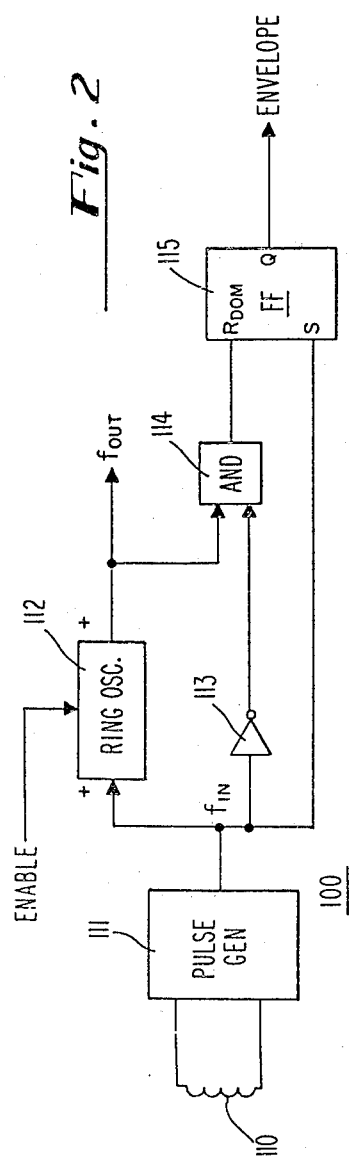
FIG. 2 is a block diagram showing the logical arrangement of the fast programmer circuit 100.

Referring now to FIG. 2, there is seen a block diagram showing the logical arrangement of the fast programmer circuit 100. A coil 110 picks up the 600 Hz signal from transmitter 96 and supplies it to pulse generator 111. Generator 111 converts the sinusoidal 600 Hz signal into a 600 Hz squarewave, and provides amplification as needed. The output, designated $f_{in}$, is connected to ring oscillator 112, through inverter 113 to a first input terminal of AND gate 114, and to the set terminal of flip-flop 115. The ring oscillator is designed to provide an output $f_{out}$ at the frequency of $f_{in}$ as long as $f_{in}$ is within a predetermined tolerance of the natural frequency of ring oscillator 112. Since oscillator 112 is a ring oscillator, it will continue to oscillate following termination of $f_{in}$, but will stop when the enable signal is removed (for the pacer embodiment, at the end of the refractory interval). Oscillator output $f_{out}$ is connected to the second input of AND gate 114. Since $f_{in}$ is a squarewave, and assuming that $f_{out}$ is likewise a squarewave in phase with $f_{in}$, the two inputs to AND gate 114 are always opposite so long as $f_{in}$ is present, such that there is always a low input to one input of AND gate 114 and no output from the AND gate as long as there is an $f_{in}$ signal. However, if there is no $f_{in}$ signal, corresponding to the absence of any modulation on the magnetic program signal, then the output of inverter 113 is high and there is an output from AND gate 114. This output is connected to the reset terminal of flip-flop 115, which is a reset-dominated flip-flop. It is thus seen that whenever $f_{in}$ is present, there is no signal on the reset terminal and the flip-flop is set by the first high level of the $f_{in}$ signal, providing a logic 1 output at terminal Q. As long as $f_{in}$ is present, there is no reset signal, and the output of flip-flop 115 stays high. However, as soon as modulation ceases and there is no $f_{in}$ signal, the flip-flop is reset and the output goes low. Accordingly, the flip-flop provides an output which corresponds to the envelope of the magnetic 600 Hz signal, being at a logic 1 when the 600 Hz signal is present and at a logic 0 in the absence of the 600 Hz signal. Thus, the circuit as shown in block diagram form of FIG. 2 provides the two outputs utilized for fast programming, namely the Q output which represents the program signal envelope, and the $f_{out}$ output which is utilized to provide timing pulses to the programmer logic.

Figure 3:
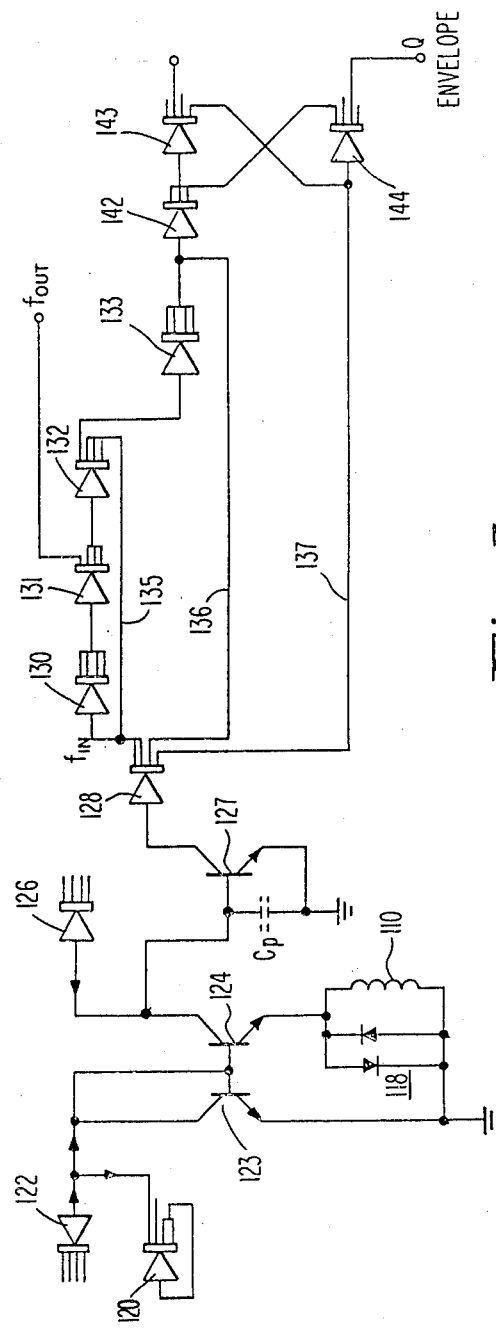
FIG. 3 is a detailed circuit diagram of the fast programmer circuit 100.

Referring now to FIG. 3, there is shown a detailed circuit diagram which provides the functions of the block diagram circuit of FIG. 2. I²L gate 122 has open circuited collectors, and by using a 10 na injector current, it provides a 10 na current source. I²L gate 120 is connected as shown to provide a 5 na sink, whereby 5 na goes into the current mirror circuit comprising transistors 123 and 124. The emitter of transistor 124 is connected to ground through pickup coil 110 and a pair of protection diodes 118. Coil 110 is designed to sense the presence of the externally applied 600 Hz magnetic signal, and is conveniently constructed of about 100 turns providing an effective area of about 5 cm². Coil 110 has a very low impedance, such that it only develops a few mv across it. This provides a high sensitivity current measuring circuit. The collector of transistor 124 is connected to I²L gate 126 which provides a 10 na current source in the direction as indicated. Thus, under normal circumstances, and assuming that the current mirror is balanced, the 10 na from source 126 divides, and 5 na goes through transistor 124 and 5 na is inputted to transistor 127, holding it in conduction.

In practice, in the absence of a magnetic field transistor 127 is conducting, holding the input to I²L gate 128 at logic 0, which in turn produces a logic 1 at its output. One collector of gate 128 is connected through line 137 to the input of I²L gate 144, which provides the envelope output. Therefore, in the absence of a detected 600 Hz signal, the output is held at a 0 logic level. When a 600 Hz signal is sensed at coil 110, the current mirror 123-124 is caused to be out of balance, thereby varying the current into the base of transistor 127, turning it on and off. This in turn causes gate 128 to turn on and off, thereby providing a 600 Hz logic signal at its collectors, which is designated as $f_{in}$.

I²L gates 130, 131 and 132, in combination with the feedback path 135 connecting 3 collectors of gate 132 with the input of gate 130, comprise a ring oscillator. The oscillator acts like conventional ring oscillators, the positive feedback being provided by the signal shift contributed by the odd number of gates as well as the delay contributed by each I²L gate. In practice, the injector current applied to each I²L gate sets the delay time, and accordingly determines the minimum frequency which can be used to drive the ring oscillator. The injector current also sets the charge-current capacitance of each gate (not shown), thereby determining the maximum drive frequency to which the ring oscillator will respond. In practice, if the input frequency gets too low, no output appears at the Q terminal, but rather $f_{in}$ is simply passed through. If $f_{in}$ is too high, the effective charge current capacitor $C_p$ at the input, shown in dashed lines, acts as an effective short circuit, holding the transistor 127 in an off condition, whereby the input to gate 128 stays at logic 1 and there is no $f_{out}$ signal. Accordingly, the circuit acts as an extremely sharp bandpass filter, providing the desired outputs only for a small range of frequencies around the natural frequency of the ring oscillator.

Two of the collectors of I²L gate 128 are connected to the input of gate 130, thereby connecting the $f_{in}$ signal to drive the oscillator. A third collector of gate 128 is connected by line 136 to the input of gate 142, and a collector of gate 132 is also connected through an inverter gate 133 to the input of gate 142, providing a wired-AND signal to that input. This is the equivalent of the AND gate 114 as shown in FIG. 2. The fourth collector of gate 128 is connected along line 137 to the set terminal of flip-flop 143, 144, the reset terminal of which is the output of gate 142.

In practice, whenever a 600 Hz magnetic signal is present, a signal is provided as designated at $f_{out}$. At the same time, the wired-AND input to gate 142 is held at a logic 0, such that the output of gate 142 is a logic 1. This causes the envelope output at terminal Q to go high. Since the flip-flop made up of gates 143, 144 is reset dominated, and the input to the reset terminal (the output of gate 142) stays high, the output at terminal Q stays high. If, however, the 600 Hz modulation signal is absent, then the input to gate 144 is held high, causing the envelope signal to go low. However, the $f_{out}$ signal is maintained due to the continuing oscillation of the ring oscillator, until the circuit is disenabled at the end of the pacer refractory interval. This is done, for example, by disconnecting the injector current from the oscillator gates following timeout of the refractory interval.

FIG. 3 thus provides a means for picking up an externally transmitted signal, and providing both a very sharp bandpass filter and an envelope detector. It is accordingly appreciated that the circuit has many applications in radio type circuits, in addition to the application as illustrated herein.

To illustrate the operation of the pacer embodiment, consider a program arrangement (i.e., sequence of encoded signals) suitable for use with this invention. The program arrangement is discussed first for the slow programming, wherein the simple magnet is used, and then for the fast programming. While the total time required for programming in the two different modes as illustrated will be very different, it is recognized that the relative timing is the same, and that the logical arrangement of the program signals is the same in both cases, thereby permitting the single programmer logic circuit 48 to decode both the fast and slow sequences of program signals.

For programming a change in rate, a "key" or first sequence of magnetic on-off signals is applied as follows:

a. Following the absence of the magnetic signal for 4 beats or more, apply the magnet for an interval less than 2 pacer pulse intervals (corresponding to heart beats, either natural or stimulated);

b. remove the magnet for an interval less than 3 pacer pulse intervals;

c. apply the magnet for an interval less than two pacer pulse intervals; and d. remove the magnet for an interval of 4 pulse intervals or more.

Following this, the key has been entered and the pacer is then conditioned to be re-programmed either up or down. To step the rate up by one unit (e.g. 5 bpm), the following additional program sequence is entered:

a. Apply the magnet for a duration greater than or equal to 4 pulse intervals;

b. remove the magnet for a duration greater than or equal to 4 pulse intervals and less than 8 pulse intervals; and c. apply the magnet for more than 2 pulse intervals.

At this point, logic circuit 48 produces an output which causes the oscillator to go up in rate by 5 bpm. To lower the rate, the same procedure is followed except that the last time period during which the magnet is removed is for a duration equal to or greater than 8 pulse intervals and less than 12 pulse intervals.

During slow programming using the illustrative program arrangement as set forth above, the magnet signal is communicated through to the M terminal of programmer logic circuit 48 due to the closing and opening of reed switch 40, whereas interval signals from the oscillator (representing either the timing out of the oscillator when in the asynchronous mode or the resetting of the oscillator when the inhibit mode) are connected to the O terminal of circuit 48. The physician counts the pulse intervals by simply monitoring the pulse of the patient, which is done by looking at an EKG or feeling the patient's pulse.

For the slow program arrangement, or format, as illustrated, the procedure takes at least 25 pulse intervals to cause a step up, and at least 29 pulse intervals to cause a step down. By contrast, during the fast programming, the entire program arrangement is transmitted and processed within a refractory interval. For the fast programming, the basic time interval is defined as the time period of the 600 Hz signal, i.e., about 1.66 ms. For the automatic fast programming, the envelope of the 600 Hz modulation, which appears at the Q terminal of circuit 100, has the same time relationship to the $f_{out}$ signal as that just described for the magnet and oscillator pulses in the slow programming mode. In other words, by way of illustration, for increasing the pacer rate by one step, the automatic fast program arrangement is as follows:

a. A steady DC magnetic field is provided throughout transmission of the program signals;

b. the Q output is a logic 1 for a time period corresponding to less than 2 cycles of the 600 Hz signal;

c. the Q output is a logic 0 for a time period corresponding to less than 3 cycles of the 600 Hz signal provided at the $f_{out}$ terminal;

d. the Q terminal is a logic 1 for a time period corresponding to less than 2 cycles of the 600 Hz signal;

e. the Q output is a logic 0 for a time period corresponding to more than 4 cycles of the 600 Hz signal;

f. the Q output is a logic 1 for a time period equal to or greater than 4 cycles of the 600 Hz signal;

g. the Q output is a logic 0 for a time period corresponding to 4 or more cycles of the 600 Hz signal and less than 8 cycles of the 600 Hz signal;

h. the Q output is a logic 1 for a time period corresponding to at least 2 cycles of the 600 Hz signal.

Since the $f_{out}$ terminal of the fast programmer circuit 100 is continuously providing a 600 Hz signal from the time that the Q terminal first goes to a logic 1, it is seen that the time coincidence of the signals applied to the M and O terminals of circuit 48 is the same as in the slow program mode. Since the programmer logic 48 comprises simply conventional logic circuitry which compares and counts the signals received at the O terminal with respect to the logic level at the M terminal, it makes no difference whether the entire program sequence is received in about 30 seconds (as for slow programming) or less than half a second (as for fast programming). In either event, as long as the relationship between the signals inputted at the two terminals meets the program arrangement, the pacer is successfully reprogrammed in accordance with the encoded program signal.

As used in this specification "high frequency" or "relatively high frequency" means a frequency higher than the manually generated slow magnetic signal. A high frequency of 600 Hz is used because of convenience in designing the ring oscillator, and because this is fast enough to permit delivery of the entire program signal during the pacer refractory period. Of course, higher and lower "high frequency" magnetic signals may be used. In any event, the pacer of this invention is adapted for programming with program signals of 2 or more different rates. It thus provides redundancy since it can be programmed by 2 or more different external transmitters.

I claim:

1. A pacer adapted to be programmed by either a fast type program signal having a relatively short program length or a slow type program signal having a relatively long program length, said pacer having stimulus means for generating stimulus signals for delivery to a patient's heart and having one or more programmable operating parameters, said pacer having receiving means for receiving said fast and slow type program signals from external to said pacer and control means for controlling said one or more parameters with control signals derived from said received program signals, said pacer being characterized by comprising means for processing said received signals to derive said control signals therefrom when said received signals conform to a predetermined program arrangement, said processing means having a common logic circuit utilized in said processing of received signals of both fast and slow type.

2. The pacer as described in claim 1, wherein said slow type signal is an on-off magnetic signal having a total duration extending over a plurality of patient heartbeats.

3. The pacer as described in claim 1, wherein said fast type signal comprises an automatically generated magnetic signal having a modulated relatively high frequency component and a total time duration limited to the refractory interval of the pacer.

4. The pacer as described in claim 1, wherein said processing means comprises a common logic circuit having two inputs for receiving two separate input signals, with means for deriving at least one of said input signals from the received program signal.

5. The pacer as described in claim 1, wherein said common logic circuit comprises means for time comparing said received signals with the timing of said stimulus means and for producing a control signal when a said received signal has a predetermined time relation to the timing of said stimulus means.

6. The pacer as described in claim 5, wherein said processing means comprises high frequency circuit means for detecting the presence of a relatively high frequency signal component in a received program signal and for producing an output representing the presence of said relatively high frequency component.

7. The pacer as described in claim 6, wherein said common logic circuit has a first input terminal connected to said stimulus means for receiving a signal representative of the timing of said stimulus means and a second input switchably connected to said receiving means and to said high frequency circuit means.

8. The pacer as described in claim 1, wherein said common logic circuit has two input terminals, said logic circuit performing the function of providing a control signal when the timing of the signals on the respective two input terminals conforms to a predetermined program arrangement.

9. The pacer as described in claim 1, wherein said means for processing comprises an envelope detector circuit detecting the presence of a relatively high frequency signal component in said fast type program signal, said envelope detector circuit comprising a ring oscillator.

10. A pacer adapted to be programmed by any one of a plurality of different predetermined program signals of respective different rates, one of said signal being a slow magnetic signal such as can be generated manually with a simple magnet applied in the vicinity of said pacer, said pacer having stimulus means for normally generating stimulus signals at a predetermined rate for delivery to a patient's heart, and stimulus means having at least one programmable operating parameter, said pacer having receiving means for receiving said plurality of program signals from external to said pacer and control means for controlling said at least one parameter with control signals derived from said received program signals, said pacer comprising processing means for processing any one of said received program signals at a time to derive said control signals therefrom when one of said received signals conforms to a predetermined program arrangement, said processing means having timing signal means for providing reference timing signals and logic means for determining when one of said received signals has a predetermined time relationship with said reference timing signals such as to constitute said predetermined program arrangement.

11. A pacer adapted to be programmed by either a fast type program signal having a relatively short program length or a slow type program signal having a relatively long program length, said pacer having stimulus means for generating stimulus signals for delivery to a patient's heart and having one or more programmable operating parameters, said pacer having receiving means for receiving said fast and slow type program signals from external to said pacer and control means for controlling said one or more parameters with control signals derived from said received program signals, said pacer comprising:
  a. reference timing means for providing reference timing signals corresponding to both said fast and slow program signals; and
  b. means for determining the time relationship of said received signals with said timing signals and for deriving said control signals equally from said fast and slow program signals whenever a predetermined time relationship is determined.

* * * * *